(12) United States Patent
Miller

(10) Patent No.: US 9,521,843 B2
(45) Date of Patent: Dec. 20, 2016

(54) PRODIAMINE-COATED FERTILIZER AND METHOD OF MANUFACTURE

(71) Applicant: Lawrence A Miller, Brookfield, CT (US)

(72) Inventor: Lawrence A Miller, Brookfield, CT (US)

( * ) Notice: Subject to any disclaimer, the term of this patent is extended or adjusted under 35 U.S.C. 154(b) by 55 days.

(21) Appl. No.: 14/230,934

(22) Filed: Mar. 31, 2014

(65) Prior Publication Data

US 2014/0213457 A1    Jul. 31, 2014

Related U.S. Application Data

(63) Continuation-in-part of application No. 13/726,061, filed on Dec. 22, 2012, now Pat. No. 8,815,776.

(60) Provisional application No. 61/808,170, filed on Apr. 3, 2013.

(51) Int. Cl.
*A61K 9/16* (2006.01)
*A61K 9/50* (2006.01)
*A01N 33/18* (2006.01)

(52) U.S. Cl.
CPC .................................... *A01N 33/18* (2013.01)

(58) Field of Classification Search
None
See application file for complete search history.

(56) References Cited

U.S. PATENT DOCUMENTS

2007/0163317 A1\* 7/2007 Birthisel ............... A01N 25/12
                                                            71/64.07
2010/0113272 A1\* 5/2010 Dunne et al. ................. 504/148
2010/0279865 A1\* 11/2010 Cosky et al. ................. 504/124

FOREIGN PATENT DOCUMENTS

JP            07109192      \*   4/1995
JP            407109193     \*   4/1995

\* cited by examiner

*Primary Examiner* — Alton Pryor
(74) *Attorney, Agent, or Firm* — Christopher G. Hayden; Hayden Stone PLLC

(57) ABSTRACT

An herbicidal concentrate composition that contains Prodiamine herbicide for application to a granular carrier such as a fertilizer granule, or a granule to be mixed with granular fertilizer.

20 Claims, No Drawings

PRODIAMINE-COATED FERTILIZER AND METHOD OF MANUFACTURE

CROSS-REFERENCE TO RELATED APPLICATIONS

This application claims priority as a CIP to Provisional application 61/808,170 filed Apr. 3, 2013, and also as a CIP to application Ser. No. 13/726,061, titled Herbicidal Compositions and Methods of Use Thereof filed on Dec. 22, 2012, which application claims priority as a CIP to Provisional application No. 61/579,662 filed Dec. 23, 2011, titled Herbicidal Compositions and Methods of Use Thereof, each or the above mentioned documents of which are incorporated by reference herein for all allowable purposes.

FIELD OF THE INVENTION

The invention relates to a concentrate for manufacturing a prodiamine-coated carrier, for example a prodiamine-coated fertilizer granule, and use of the concentrate to manufacture said prodiamine-coated fertilizer granule.

BACKGROUND OF THE INVENTION

The statements in this section merely provide background information related to the present disclosure and may not constitute prior art.

It is generally known to use certain selective herbicides with fertilizers. The combination is so useful that there are a number of products that combine selective herbicides with fertilizers, including for example Scott's Step 1 Crabgrass Preventer Plus Fertilizer which contains about 1.22% pendimethalin. For solid herbicides, this selective herbicide is either included in the fertilizer as a separate granular material admixed with the fertilizer or even as very small particulates of herbicide coating fertilizer granules, where said particulates are adhered to the fertilizer using a "white oil," that is, an inert sticky oil. Said product has several drawbacks, including the need to mill solid herbicide to less than 10 microns, often as little as 1 micron, and the propensity of a small amount of the herbicide to wipe off and adhere to hands, clothes, or fertilizer spreaders.

What is needed is an alternative herbicide for combination with fertilizer for use on turf. Further, what is needed is a manufacturing process to prepare single applications of the selective herbicide/fertilizer mixture that addresses the issues of small herbicide particles disposed on larger granules.

SUMMARY OF THE INVENTION

One aspect of the invention of this application relates to a method of manufacture of a granular fertilizer carrier containing prodiamine thereon by use of a solvent-based prodiamine concentrate sprayed directly on fertilizer granules, and the resulting product. Another aspect of this invention is a method of making the combination formulation, including use of a solvent-based prodiamine concentrate for the manufacture of a fertilizer and other granular prodiamine carriers.

High-concentration prodiamine concentrates are useful for manufacturing such products, which are typically granular. The solvent-based prodiamine concentrate comprises, consists essentially of, or alternatively consists of 15% to 60%, more typically 20% to 45%, preferably 25% to 40% by weight of prodiamine, the remainder typically comprising solvents as described herein. The concentrate is preferably a solution, and most if not all of the solvents are preferably sufficiently volatile such that the solvents can be removed in the manufacturing process.

Generally, higher prodiamine concentrate formulations are preferred. In some instances, some formulations of a prodiamine granular product provide a low concentration granular product, and for this embodiment a solvent-based prodiamine concentrate less than 25% can be useful.

A particularly good solvent for making the concentrate is n-methyl pyrrilidinone (NMP, or N-methyl pyrrolidone), which forms a maximum solubility of ≈40% at room temperature. Because the preferred granular products made by the methods of this invention do not themselves comprise the solvent, other solvents can be utilized, and a heated concentrate and/or a mixture of solvents capable of dissolving or containing greater than 40% by weight prodiamine is useful in the method of making granular prodiamine products, including prodiamine on inert carriers and prodiamine coated onto fertilizer. Other particularly useful solvents for making high-concentration (e.g., greater than 30% by weight prodiamine) include other alkyl pyrrolidinones, for example n-octyl pyrrilidinone, and acetone.

The granular prodiamine product is formed by applying the solvent-based prodiamine concentrate onto the grains, and then evaporating off the solvent. Prodiamine coated on the exterior of fertilizer, with optionally another inert coating thereon, are preferred. Fertilizers are often formulated for slow release, but it is advantageous to get the prodiamine into the soil rapidly, though it then can remain in the soil for most of the season. Coating prodiamine on the exterior of fertilizer ensures getting the prodiamine to the plants where it can become immediately active.

The method of manufacture includes the steps of 1) providing a granular carrier, particularly a fertilizer granule adapted for use in turf or a lower density carrier such as paper fiber, corn cob, and the like; 2) wetting the granular carrier with the solvent-based prodiamine concentrate; 3) removing the solvent; and optionally 4) coating the granular product with an outer coating to improve flowability, hydroscopic properties, or to insulate the prodiamine from incidental contact with a person applying the combination prodiamine product to turf. If a different carrier, for example a low density carrier, is used, the treated carrier is admixed with granular fertilizer.

The solvent-based prodiamine concentrate comprises, consists essentially of, or consists of 15% to 60%, more typically 20% to 40% by weight prodiamine dissolved in one or more polar aprotic solvents. In a preferred mode the concentrate comprises, consists essentially of or alternatively consists of 25% to 42%, preferably 30% to 40%, for example between 34 and 39%, by weight prodiamine dissolved in one or more polar aprotic solvents, where N,M-pyrrolidinone (also typically called N-methypyrrolidone or NMP), other alkyl pyrrolidinones, acetone, or mixture thereof comprises at least 50% by weight of the polar aprotic solvents.

To get to highest concentrations, NMP is advantageously used, preferably additionally maintaining the concentrate at a higher temperature. At room temperature the maximum solubility of prodiamine in NMP is between 39% and 40% by weight. For manufacturing contingencies, the concentrate can be made to not contain the maximum dissolvable. For example, a concentrate comprising, consisting essentially of or alternatively consisting of NMP and prodiamine may only contain 35 to 38% by weight prodiamine, to allow for stability in the event the concentrate is stored. Other solvents which may additionally be used comprise dimethylformamide (DMF) and dimethylsulfoxide (DMSO). Dimethylacetamide is expected to have good solvating properties and could be useful in controlled manufacturing conditions. Dimethylformamide is also expected to have good solvating properties but use is highly restricted, so, even though the concentrate is used in manufacturing, this solvent is not preferred.

In alternative embodiments the concentrate may comprise, consist essentially of, or consist of prodiamine, the aprotic solvent(s), and one or more of gamma-Butyrolactone or a fatty acid dialkylamide solvent. In another embodiment the concentrate may comprise prodiamine, the aprotic solvent(s), and a fatty acid dialkylamide solvent.

One optional adjuvant is a surfactant that facilitates movement of the prodiamine to the soil or that facilitates uptake of prodiamine by targeted plants. Exemplary surfactants are presented herein and are known in the art.

The concentrate is sprayed, rolled with, or otherwise contacted with a carrier, the colvent-based concentrate advantageously wetting the carrier. In some embodiments, the concentrate is sprayed onto the carrier, which is then dried.

The carrier may be any agriculturally or horticulturally acceptable carrier. Examples would include but are not limited to ground corncobs, peanut hulls, limestone, clay, or granulated paper fiber. Ground corn husks, granulated paper fiber, or ground shell are often used if a light weight carrier is desired. However, for the granular preemergence herbicide it is desirable to get the herbicide product to the soil where the weeds are emerging. Coating the fertilizer onto a higher bulk density carrier is therefore preferred, and we have found granular fertilizer products are ideally suited to serve as a carrier for the prodiamine. The fertilizer product may be mineral-based or organic-based, often with inert granular components such as limestone, clay, ground corncobs or peanut hulls, granulated paper fiber, or other suitable carriers added to the fertilizer to improve its formulation characteristics.

In one preferred embodiment, the carrier can be pellets comprising or consisting essentially of a fertilizer. Any fertilizer would be useful, but especially useful would be fertilizers adapted for use in turf, as is known to one of ordinary skill in the art. The fertilizer can be fast release or slow release, containing e.g., methylene urea or sulfur-coated urea, or a polymer-coated fertilizer.

The concentrate may additionally comprise dissolved therein polymer which impart a slow dissolving or release characteristic to the carrier, especially the fertilizer. Simple coatings can include for example starch of any of the polymers known (typo) to those of ordinary skill in the art. The coating can be present dissolved or suspended in the concentrate in amounts from 0.01% to 15% by weight of the concentrate. In an alternative embodiment, such material may be disposed in a layer between the carrier and the prodiamine, or in a layer deposited over the layer of prodiamine, or both.

A carrier that has had the concentrate of the invention sprayed thereon can be further coated with coatings that impart slow release properties, anti-caking properties, and/or easy-flowing properties, as is known to those of ordinary skill (typo) in the art. This second coating may be more effective than coatings dissolved in the carrier to insulate people from incidental contact, for example by handling the fertilizer.

Embodiments of the invention relate to use of a non-aqueous solvent-based concentrate formulation for improved herbicidal protection applied to a carrier, which consists essentially of
  (a) 10 weight percent to 40 weight percent of Prodiamine active herbicidal ingredient;
  (b) optionally 1 weight percent to 60 weight percent of a fatty acid dialkylamide solvent;
  (c) 5 weight percent to 60 weight percent of a polar aprotic organic solvent, for example wherein the polar aprotic organic solvent consists of, consists essentially of, or comprises N,M-pyrrolidinone; and
  (d) optionally 1 weight percent to 12 weight percent of a surfactant, for example an alkyl-alkoxylate-based emulsifier, typically a alkyl-based EO-containing block copolymer emulsifier, for example an Ethylene oxide/Propylene oxide alkyl (e.g., butyl) block copolymer, a hydrophilic non-ionic emulsifier, typically a ethoxylated fatty alcohol, for example a tridecyl alcohol hydrophilic non-ionic emulsifier; and/or fatty acid benzene solfonate, particularly calcium salts of dodecyl-benzenesulfonate.

Prodiamine is a selective herbicide having a formula N3,N3-di-n-propyl-2,4-dinitro-6-(trifluoromethyl)-m-phenylenediamine. Prodiamine is typically used as a pre-emergence herbicide for preferably season long control of grass and broadleaf weeds, including crabgrass. Prodiamine is typically used at application rates of between 0.25 and 1.5 lb ai/A (0.28-1.68 kg/ha), but typically it would be used at 0.5 to 1.0 lb ai/A (0.56-1.12 kg/ha).

We found alkyl pyrrolidinones, particularly N-methylpyrrolidinone ("NMP"), to be particularly useful to formulate a high-concentration prodiamine EC, that is, greater than 10% by weight active ingredient. Dimethylsulfoxide is useful, but has less than half the solubilizing ability as NMP. Use of DMSO in the absence of NPM will result in a practical limitation of less than 10% prodiamine in the EC. Other solubilizing solvents include fatty acid amide solvents such as N,N-dimethylcaprylamide (Cognis Agnique KE-3658) and N,N-dimethyloctanamide (Halcomid M8-10). These solvents are "green," but use in the absence of NPM will result in a practical limitation of less than about 10% prodiamine.

The invention also relates to the use of such a solvent-based high prodiamine concentrate composition as an intermediate in manufacture of granular herbicide. Polar organic solvents such as N-methypyrrolidone (NMP), dimethylformamide (DMF) and dimethylsulfoxide (DMSO) have been used to impart good solubility properties prodiamine. Surprisingly, gamma-Butyrolactone also also shows solvating capacity near that of DMSO and the fatty amide solvents. Dimethylacetamide is expected to have good solvating properties but was not tested. Acetone can be useful because while if's flash point is low, giving a safety concern, this solvent is readily evaporated from the carrier. Dimethylformamide is also expected to have good solvating properties but use is highly restricted.

Accordingly, it is an object of the present invention to produce and utilize a stable, low phytotoxic concentrate formulation of prodiamine. We believe a concentrate utilizing one or more fatty amide solvents, e.g. an optionally alkylated C8 to C18 fatty amide, gamma-Butyrolactone, DMSO, or combination can provide a formulated concentrate with an acceptable amount of prodiamine, say 5% to 15%. NMP (CAS 872-50-4) provides superior solvating capacity, more than twice other solvents tested.

Embodiments of the invention relate to a concentrate formulation for improved herbicidal protection which consists essentially of
- (a) 10 weight percent to 30 weight percent of Prodiamine active herbicidal ingredient
- (b) 30 weight percent to 60 weight percent of a fatty acid dialkylamide solvent
- (c) 10 weight percent to 30 weight percent of a polar aprotic organic solvent
- (d) optionally 5 weight percent to 8 weight percent of an alkyl based block copolymer emulsifier;
- (e) optionally 2 weight percent to 5 weight percent of an trialkyl alcohol hydrophilic non-ionic emulsifier; and
- (f) optionally, up to 2 weight percent of an anionic emulsifier, and to the use of such an concentrate composition to form granular herbicide/fertilizer combinations.

An alternative concentrate formulation for use in manufacturing a granular herbicide is a concentrate which does not contain alkyl pyrrilodinones, for example an concentrate which consists essentially of
- (a) 10 weight percent to 40 weight percent of Prodiamine active herbicidal ingredient;
- (b) 30 weight percent to 60 weight percent of acetone;
- (c) 10 weight percent to 30 weight percent of a polar aprotic organic solvent selected from DMSO and gamma-Butyrolactone:
- (d) optionally 2 weight percent to 8 weight percent of an alkyl based block copolymer emulsifier;
- (e) optionally 2 weight percent to 8 weight percent of a trialkyl alcohol hydrophilic non-ionic emulsifier; and
- (f) optionally, up to 2 weight percent of an anionic emulsifier.

A preferred embodiment of the invention is a non-aqueous concentrate formulation for improved herbicidal protection which consists essentially of
- (a) 15 weight percent to 40 weight percent, preferably 20 to 30 weight percent, of Prodiamine active herbicidal ingredient;
- (b) 20 weight percent to about 60, for example 25 to 45, weight percent of N,M-pyrrolidinone;
- (c) optionally 1 weight percent to 50, for example 5 to 30 weight percent, of a fatty acid dialkylamide solvent;
- (d) optionally 2 weight percent to 6 weight percent of an alkyl based block copolymer emulsifier;
- (e) optionally 1 weight percent to 5 weight percent of an trialkyl alcohol hydrophilic non-ionic emulsifier;
- (f) optionally 0.1 to 2 weight percent of an anionic emulsifier such as a alkyl sulfonate or alkyl aryl sulfonate.

A preferred embodiment of the invention is use of a non-aqueous concentrate formulation for improved herbicidal protection which consists essentially of
- (a) 15 weight percent to 40 weight percent of Prodiamine active herbicidal ingredient;
- (b) 25 to about 60 weight percent of N,M-pyrrolidinone;
- (c) optionally 40 to 50 weight percent, of a fatty acid dialkylamide solvent.

This embodiment shows excellent stability.

Generally, the term "consists essentially of" means there are no other herbicidal active ingredients in the concentrate.

Fenoxaprop p-ethyl (we often refer to the herbicide as "fenoxaprop") is a postemergence graminicide used on cool-season turfgrasses to control crabgrass and other annual grass weeds. It is known to mix fenoxaprop-p-ethyl with prodiamine, providing quick anti-crabgrass effect of fenoxyprop-p-ethyl with long term preemergence effect of prodiamine. Fenoxaprop is best provided to the foliage, so if prodiamine and fenoxyprop are both coating the granule, advantageously the fenoxaprop-p-ethyl is released from the granule immediately on application off sufficient water. In the above formulations, fenoxaprop-p-ethyl can replace some of the prodiamine, for example an amount of fenoxaprop wherein the weight ratio of prodiamine to fenoxyprop is in the range of 3:1 to about 8:1, more preferably about 4:1 to about 6:1, for example about 5:1. Alternatively fenoxyprop can be added to a low density carrier and admixed into the fertilizer, as fenoxyprop has foliar activity.

An alternative embodiment of the invention relates to application onto a carrier of a non-aqueous concentrate formulation for improved herbicidal protection which consists essentially of
- (a) 10 weight percent to 33 weight percent, preferably 12 weight percent to 30 weight percent, more preferably between 15 weight percent to 25 weight percent weight percent of Prodiamine (99.4% active) herbicidal ingredient;
- (b) 2 weight percent to 10 weight percent, preferably 3 weight percent to 8 weight percent, more preferably between 3 weight percent to 6 weight percent weight percent of fenoxaprop-p-ethyl (98.5% active, "fenoxyprop") herbicidal ingredient;
- (c) 20 weight percent to 70 weight percent of a solvent selected from fatty acid dialkylamide solvents, gamma-butyrolactone, polar aprotic solvents, or mixtures thereof;
- (d) and optionally 0.5 to 10 percent by weight of surfactants, starches, and the like.

The material is primarily intended as a once-per-season treatment of turf to control crabgrass. Generally, the weight ratio of prodiamine to fenoxyprop is in the range of 3:1 to about 8:1, more preferably about 4:1 to about 6:1, for example about 5:1. There must be sufficient fenoxyprop to effect a kill on existing crabgrass. The application timing and conditions of applying these herbicides are known in the art, and best efficacy of fenoxaprop is obtained by early application (before three tiller stage) and to well watered turf. Too much prodiamine, or too late an application of the herbicide, and the preemergent herbicide may interfere with fall over-seeding programs.

All percentages and the term "w/w" used herein unless specifically stated are percent by weight, and all component amounts recited as "parts" are parts by weight and are usually on a basis of parts per part of the active ingredient. The term "ppm" is parts per million by weight. When salts of components are mentioned, unless otherwise specifically stated, the composition can contain the acid form of the component, one or more salts of the component, or any mixture thereof.

The aprotic solvent is preferably a pyrrolidone such as NMP, though one or more of dimethylsulfoxide (DMSO), dimethylformamide, and gamma-Butyrolactone alone or in mixtures, including mixtures with NMP, are useful. Various useful and incidental solvents are shown below, with the measured solubility of each of the active ingredients. The units for solubility below are grams of active ingredient per gram of respective solvent. All measurements were based on physical clarity and were performed at 22 degrees C.

| Solvent | Prodiamine | Fenoxaprop-p-ethyl |
|---|---|---|
| N-methyl pyrrolidinone (NMP) | 0.68 | 1.04 |
| Dimethylsulfoxide ("DMSO") | 0.24 | 0.72 |

-continued

| Solvent | Prodiamine | Fenoxaprop-p-ethyl |
|---|---|---|
| Aromatic 150 (Aromatic Naphtha Hydrocarbon) | 0.08 | 0.36 |
| Aromatic 200 (Aromatic Naphtha Hydrocarbon) | 0.07 | 0.24 |
| Glycol Ether EB (Diethylene glycol monubutyl ether) | 0.02 | 0.12 |
| Carbitol TM (Diethylene glycom monomethyl ether) | 0.01 | 0.12 |
| Jefsol 1555 Proprietary Solvent (Carbonate) | 0.004 | <0.12 |
| Glycol DPM (Dipropylene glycol methyl ether) | 0.008 | <0.12 |
| Halcomid M8-10 (fatty acid dialkylamide solvent) | 0.24 | 0.36 |
| Exxol D110 (Paraffin Hydrocarbon) | <0.02 | <0.04 |
| Agnique KE-3658 (fatty acid dialkylamide solvent) | 0.24 | 0.36 |
| BLO (Gamma-Butyrolactone) | 0.25 | 0.58 |
| DEGEE (Diethylene glycol monoethyl ether) | 0.05 | 0.08 |

It can be seen that each polar aprotic solvent, NMP and DMSO, provide reasonable solubility, though NMP is far and away the superior solvent.

Fatty amides, also called "fatty acid solvents" in this application, are amides formed from a fatty acid and an amine, of which many are known. Preferred are di-substituted fatty acid amides, which include as non-limiting examples N,N-dimethylcaprylamide (available from Cognis as Agnique™ KE-3658), and N,N-diethyloctanamide (available as Halcomid™ M8-10). These compounds can fully or partially replace aprotic solvents, and the solvating capacity approaches that of less-preferred aprotic solvents such as DMSO and gamma-Butyrolactone, that is, 0.24 to 0.25 grams prodiamine per gram solvent. A mixture of C8 and C10 fatty acid dimethylamide, (CAS 1118-92-9 and 14433-76-2) are useful.

The alkyl-alkoxylate-based emulsifier is typically an alkyl-based EO/PO-containing block copolymer emulsifier, for example an Ethylene oxide/Propylene oxide alkyl (e.g., butyl) block copolymer. It is possible to use suitable co-polymers of ethylene oxide and propylene oxide, such as ABA or BAB block copolymer or BA block copolymers. The alkyl group can range from C3 to C7, for example. A preferred group of ethylene oxide/propylene oxide block copolymers for use in the compositions of this invention are butyl based poly(oxypropylene)poly(oxyethylene) block copolymers having an average molecular weight in a range of 2,400 to 3,500 (e.g. TOXIMUL™ 8320, Stepan Chemical Co.) Also useful is Harcros™ TDA-12.

The hydrophilic non-ionic emulsifier can be an ethoxylated alcohol. A C9 to CI8 alcohol can be used, with for example 8 to 20 EO units, for example a tridecyl alcohol hydrophilic non-ionic emulsifier. Examples include Makon™ TD-12, a tridecyl alcohol ethoxylate, POE-12 available from Stepan, or Harcros TDA-12.

Generally an anionic emulsifier can provide added emulsion stability, and alkyl sulfonates are useful for this purpose, for example a fatty acid benzene sulfonate, particularly calcium salts of dodecylbenzenesulfonate.

What is claimed:

1. A method of manufacture of a granular product coated with prodiamine, comprising
   a) providing a granular carrier,
   b) coating said carrier with a prodiamine concentrate solution comprising 25% to 45% by weight prodiamine in an aprotic solvent, and
   c) drying said coated carrier to provide a prodiamine coated carrier, wherein said granular prodiamine-coated carrier product is effective for weed control in turf and other non-agricultural sites, and wherein the aprotic solvent comprises n-octyl pyrrolidinone.

2. The method of claim 1 wherein the aprotic solvent comprises N,M-pyrrolidinone.

3. The method of claim 1 wherein the aprotic solvent comprises acetone.

4. The method of claim 1 wherein the carrier consists essentially of fertilizer granules.

5. The method of claim 1 further comprising the step of providing an effective amount of a slow-dissolving coating material dissolved or suspended in the prodiamine concentrate.

6. The method of claim 1 further comprising the step of providing an effective amount of a slow-dissolving coating material disposed in a layer between the carrier and the prodiamine.

7. The method of claim 1 further comprising coating the granular product with an outer coating to improve flowability, hydroscopic properties, or to insulate the prodiamine from incidental contact with people.

8. The method of claim 1 wherein the aprotic solvent consists essentially of n-octyl pyrrolidinone.

9. The method of claim 1 wherein the aprotic solvent contains no N,M-pyrrolidinone.

10. A method of manufacture of a granular product coated with prodiamine herbicide, comprising
    a) providing a granular carrier which is a fertilizer granule adapted for use in turf;
    b) coating the granular carrier with a solvent-based prodiamine concentrate comprising prodiamine in a solvent; and
    c) removing solvent to form a herbicide layer comprising prodiamine wherein the concentrate consists essentially of 25% to 42% by weight prodiamine dissolved in the solvent, and wherein N,M-pyrrolidinone comprises at least 50% by weight of the solvent.

11. The method of claim 10 further comprising coating the granular product with an outer coating to improve flowability, hydroscopic properties, or to insulate the prodiamine from incidental contact with a person applying the granular product to turf.

12. The method of claim 10 wherein the solvent-based prodiamine concentrate comprises 30% to 40% by weight prodiamine dissolved in the solvent.

13. The method of claim 10, wherein the concentrate additionally comprises dissolved therein a coating material which imparts a slow dissolving or release characteristic to the carrier, wherein the coating is dissolved or suspended in the concentrate in amounts from 0.01% to 15% by weight of the concentrate.

14. The method of claim 10, the granular carrier further comprises a coating which imparts a slow dissolving or release characteristic to the carrier, said coating disposed in a layer between the carrier and the prodiamine.

15. A method of manufacture of a granular product coated with prodiamine herbicide, comprising
    a) providing a granular carrier which is a fertilizer granule adapted for use in turf;
    b) coating the granular carrier with a solvent-based prodiamine concentrate comprising prodiamine in a solvent; and
    c) removing solvent to form a herbicide layer comprising prodiamine wherein the solvent comprises n-octyl pyrrolidinone and wherein the concentrate consists essentially of 25% to 42% by weight prodiamine in the solvent.

16. The method of claim 15 wherein the aprotic solvent consists essentially of n-octyl pyrrolidinone.

17. The method of claim 16 wherein the solvent contains no N,M-pyrrolidinone.

18. The method of claim 15, wherein the concentrate additionally comprises dissolved therein a coating material which imparts a slow dissolving or release characteristic to the carrier, wherein the coating is dissolved or suspended in the concentrate in amounts from 0.01% to 15% by weight of the concentrate.

19. The method of claim 15, the granular carrier further comprises a coating which imparts a slow dissolving or release characteristic to the carrier, said coating disposed in a layer between the carrier and the prodiamine.

20. A method of manufacture of a granular product coated with prodiamine, comprising
   a) providing a granular carrier,
   b) coating said carrier with a prodiamine concentrate solution comprising 25% to 45% by weight prodiamine in an aprotic solvent, and
   c) drying said coated carrier to provide a prodiamine coated carrier, wherein said granular prodiamine-coated carrier product is effective for weed control in turf and other non-agricultural sites, wherein the aprotic solvent contains at least one alkyl pyrrolidinone, but no N,M-pyrrolidinone.

* * * * *